US011622706B2

(12) United States Patent
Iwasawa et al.

(10) Patent No.: US 11,622,706 B2
(45) Date of Patent: Apr. 11, 2023

(54) BLOOD SAMPLING DEVICE

(71) Applicant: Micro Blood Science Inc., Tokyo (JP)

(72) Inventors: Hajime Iwasawa, Ossining, NY (US);
Tomoaki Nishimura, Tokyo (JP);
Shota Nemoto, Tokyo (JP)

(73) Assignee: Micro Blood Science Inc., Tokyo (JP)

( * ) Notice: Subject to any disclaimer, the term of this patent is extended or adjusted under 35 U.S.C. 154(b) by 745 days.

(21) Appl. No.: 16/610,402

(22) PCT Filed: Jun. 11, 2019

(86) PCT No.: PCT/JP2019/023139
§ 371 (c)(1),
(2) Date: Nov. 1, 2019

(87) PCT Pub. No.: WO2020/044722
PCT Pub. Date: Mar. 5, 2020

(65) Prior Publication Data
US 2022/0257156 A1     Aug. 18, 2022

(30) Foreign Application Priority Data

Aug. 30, 2018   (JP) .............................. JP2018-161403

(51) Int. Cl.
*A61B 5/15*              (2006.01)
(52) U.S. Cl.
CPC .. *A61B 5/150022* (2013.01); *A61B 5/150251* (2013.01); *A61B 5/150267* (2013.01);
(Continued)

(58) Field of Classification Search
CPC ........ B01L 3/021; B01L 3/0275; B01L 3/502;
B01L 3/565; B01L 2300/161;
(Continued)

(56) References Cited

U.S. PATENT DOCUMENTS

| 4,007,639 A | 2/1977 | Haeckel |
| 2017/0001191 A1* | 1/2017 | Biadillah ................ B01L 3/502 |

(Continued)

FOREIGN PATENT DOCUMENTS

| WO | 2016147748 A1 | 9/2016 |
| WO | 20180034032 A1 | 2/2018 |

OTHER PUBLICATIONS

Extended European Search Report dated Jan. 13, 2021 for European Patent Application No. 19797976.8.

*Primary Examiner* — David J. McCrosky
(74) *Attorney, Agent, or Firm* — Hunton Andrews Kurth LLP (57) ABSTRACT

An exemplary blood sampling device can be provided that can collect a small amount of blood and prevent blood leakage. The exemplary blood sampling device can comprise a pipette tip-shaped blood sampler having an internal space for aspirating and holding blood by the capillary action and having openings at the top and bottom, a cylindrical container capable of accommodating the blood sampler and a cap piston-shaped sealing cap for sealing the container, wherein a receiving part is provided at the bottom of the container and a locking part and a screw part are provided on the upper outer side of the container, and a mandrel extending from the inner upper surface of the sealing cap is provided and a projection and a screw part are provided on the inner side surface of the sealing cap.

15 Claims, 3 Drawing Sheets

(52) U.S. Cl.
CPC .. *A61B 5/150343* (2013.01); *A61B 5/150351* (2013.01); *A61B 5/150755* (2013.01)

(58) Field of Classification Search
CPC ..... B01L 2400/0406; B01L 2400/0688; B01L 2400/088; B04B 5/02; A61B 5/150022; A61B 5/150251; A61B 5/150267; A61B 5/150343; A61B 5/150351; A61B 5/150755

See application file for complete search history.

(56) References Cited

U.S. PATENT DOCUMENTS

| | | | |
|---|---|---|---|
| 2017/0265847 A1* | 9/2017 | Cortelazzo | .............. B01L 3/508 |
| 2018/0345276 A1 | 12/2018 | Iwasawa et al. | |
| 2019/0159710 A1 | 5/2019 | Iwasawa et al. | |

* cited by examiner

BLOOD SAMPLING DEVICE

CROSS REFERENCE TO RELATED APPLICATION(S)

This application relates to, and claims the benefit and priority from International Patent Application No. PCT/JP2019/023139 filed on Jun. 11, 2019, which claims the benefit and priority from Japanese Patent Application No. 2018-161403 filed on Aug. 30, 2018, the entire disclosures of which are incorporated herein by reference in their entireties.

FIELD OF THE DISCLOSURE

The present disclosure relates to a blood sampling device for collecting a small amount of blood.

BACKGROUND INFORMATION

It is known that modulations and diseases in a living body appear as changes in components of body fluids such as blood, urine, saliva and the like as biological reactions. Thus, by measuring and analyzing components contained in body fluids, changes in physical conditions are monitored and diseases are detected. In particular, blood tests for measuring blood components are widely performed as an effective means for examining a medical condition and as a means for health care.

As a device for collecting a small amount of peripheral blood, a blood collection tube composed of a capillary tube has been conventionally known. In addition, a capillary tube having a cylindrical structure with a capillary tube-like nozzle part has been proposed as a structure for easily taking out the blood held in the capillary tube without transferring the blood collected in the capillary tube to the reservoir (see, U.S. Pat. No. 4,007,639). Here, a cap is prepared to plug the nozzle part of the capillary tube, and after blood is collected, the nozzle of the capillary tube is plugged using the cap and placed in a cylindrical external container. Alternatively, a nozzle cap structure is prepared in the external container, and the nozzle is plugged when the capillary tube is placed in the external container. Under that state, it can be centrifuged and moved.

In addition, the present inventors have proposed a sample collection/separation device composed of a pipette tip-shaped sample collecting device, a test sample storage device and a test sample sealing cap (see International Patent Publication WO2016/147748). There, a sample collection/separation device is disclosed in which a sample collecting device holding blood collected using the capillary action is inserted into a test sample storage device and then a test sample sealing cap is attached. Furthermore, it is also disclosed that a projection that is in close contact with the bottom opening is provided on the bottom cap that seals the bottom opening of the sample collecting device.

In addition, the present inventors have proposed a blood sampling device composed of a pipette tip-shaped blood sampler, a blood container and a sealing cap (see, WO2018/034032Patent Document 3). There, a blood sampling device is disclosed in which blood is collected into a blood sampler by using the capillary action, and then blood is transferred from the blood sampler to the blood container and a sealing cap is attached.

The sample collection/separation device by the present inventors is excellent as a device for collecting a small amount of blood. Before blood collection, the sample collecting device is placed in the test sample storage device and the test sample sealing cap is closed, and the sample is transported to the user. Thereafter, at the time of blood collection, the user opens the test sample sealing cap, removes the sample collecting device from the test sample storage device, collects blood, and then inserts the blood sampling device into the test sample storage device again, and closes the test sample sealing cap to make it sealed. Thereafter, the sample collection/separation device containing blood is transported for blood examination.

In the above-described sample collection/separation device, even before blood collection, since the sample collecting device is placed in the test sample storage device and the test sample sealing cap is closed, the bottom opening (tip) of the sample collecting device is in a state of being pressed to the bottom of the test sample storage device (the bottom cap that seals the bottom opening). For this reason, the tip of the sample collecting device may be deformed during transportation, and in such a case, after collecting blood, even if the sample collecting device is again inserted into the test sample storage device and the test sample sealing cap is closed, there is a risk of incomplete sealing state. Such incomplete sealing can cause blood leakage in some cases. In particular, if the bottom cap that seals the bottom opening of the sample collecting device is provided with a projection that is in close contact with the bottom opening, the projection is likely to deform, and after collecting blood, even if the blood sampling device is again inserted into the test sample storage device and the test sample sealing cap is closed, the projection does not fit well into the bottom opening of the sample collecting device, and blood leakage is likely to occur.

Blood is transported in various environments. In some cases, it is performed not only under atmospheric pressure but also under negative pressure. Further, depending on the type of blood and the purpose of the test, there is a case where it is required that blood does not leak even under negative pressure in addition to atmospheric pressure.

OBJECT(S) AND SUMMARY OF EXEMPLARY EMBODIMENTS

In view of the above-described problems, one of the object of the present disclosure is to provide a blood sampling device that can prevent blood leakage.

One embodiment of the blood sampling device of the present disclosure comprises a pipette tip-shaped blood sampler having an internal space for aspirating and holding blood and having openings at the top and bottom, a cylindrical container capable of accommodating the blood sampler and a cap piston-shaped sealing cap for sealing the container.

In the internal space of the blood sampler, the bottom opening and the top opening communicate, and the lower part of the internal space constituting the blood holding part has a tapered shape from the bottom opening toward the top opening. The blood sampler is configured so that blood is aspirated into the internal space by the capillary action when the bottom opening is brought into contact with blood.

The container has an internal space into which the above-described blood sampler can be inserted and a receiving part at the bottom into which the tip of the blood sampler can be inserted. A locking part having a claw-like projection and a screw part are provided on the upper outer side of the container. The locking part and the screw part are arranged to be offset from each other in the vertical direction in that order from the top of the container.

The sealing cap has a mandrel extending from the inner upper surface of the sealing cap, and the mandrel is inserted into the internal space of the blood sampler in a state wherein the blood sampler is inserted into the container. A projection that engages with the projection of the locking part of the container and a screw part that can be screwed into the screw part of the container are provided on the inner side surface of the sealing cap. The projection and the screw part are arranged to be offset from each other in the vertical direction in that order from the top of the sealing cap.

The blood sampling device of the present disclosure can also be stored and transported as a set of the blood sampler, the container and the sealing cap in a separate state before blood collection, but it is preferable that the blood sampling device is stored and transported in a state wherein the blood sampler is housed in the container and the sealing cap is attached to the upper part of the container. When the sealing cap is attached to the upper end of the container in a state wherein the blood sampler is inserted, the screw part of the sealing cap and the screw part of the container come into contact with each other and serve as a stopper by which the container cannot be inserted into the sealing cap any more, and while, the projection of the locking part of the container and the projection of the sealing cap engage with each other to prevent the sealing cap from coming off, and the sealing cap is loosely fitted to the upper end of the container. Under such a state, storage and transportation can be performed.

In the blood sampling device of the present disclosure, when blood is collected using a blood sampler, then the blood sampler which is holding blood is inserted into the container and then the sealing cap is attached and rotated, as a result, the screw part of the container and the screw part of the sealing cap are screwed together, and the blood sampler is further inserted into the receiving part of the container and further the mandrel on the inner side of the sealing cap is inserted into the upper part of the blood sampler. In this state, the top opening and the bottom opening of the blood sampler are closed, and the container is sealed, and sufficient sealing is achieved. Thereby, the collected blood can be stored and/or transported more safely and easily. Before the blood collection, if the sealing cap is attached in a state wherein the blood sampler is accommodated in the container in the blood sampling device of the present disclosure, blood collection and accommodation can be carried out by performing the same step as described above after opening the loosely fitted sealing cap, taking the blood sampler out of the container and collecting blood.

In another exemplary embodiment of the blood sampling device of the present disclosure, it is preferable that two locking parts and two screw parts are provided on the upper part of the container and two projections and two screw parts are provided on the sealing cap, respectively. It is more preferable that two locking parts, two projections and two screw parts each are disposed at opposite positions across the center line.

In another exemplary embodiment of the blood sampling device of the present disclosure, a projection fitting into the bottom opening of the blood sampler is provided at the bottom surface of the receiving part of the container. By providing the projection, sealing of the bottom opening of the blood sampler becomes better.

In another exemplary embodiment of the blood sampling device of the present disclosure, the receiving part of the container is so configured that an agent is held in a part of the receiving part and if the blood sampler holding blood is inserted strongly into the container, at least a part of the agent enters the blood sampler.

In another exemplary embodiment of the blood sampling device of the present disclosure, the inner wall of the lower part of the internal space of the blood sampler constituting the blood holding part for holding collected blood is hydrophilically treated.

In another exemplary embodiment of the blood sampling device of the present disclosure, an agent is applied to the inner wall of the lower part of the internal space of the blood sampler constituting the blood holding part for holding collected blood.

In another exemplary embodiment of the blood sampling device of the present disclosure, the blood sampler has U-shaped projection(s) at the upper part, and the container has U-shaped notch(es) that fits to the U-shaped projection(s) at the upper part.

In another exemplary embodiment of the blood sampling device of the present disclosure, a step is provided on the outer periphery near the upper part of the blood holding part of the blood sampling device, and the step on the outer periphery and the inner periphery of the upper end of the receiving part of the container are configured so as to be closely fitted.

Even if the blood sampling device of the present disclosure is in a state where the blood sampler is inserted into the container and the sealing cap is attached before blood collection, the bottom opening (tip) of the blood sampler is not in a state of being pressed to the bottom of the container (the bottom of the receiving part sealing the bottom opening), there is no fear that the tip (the bottom opening) of the blood sampler is deformed. Even if the bottom of the container (the bottom of the receiving part) is provided with a projection that is in close contact with the bottom opening of the blood sampler, the projection is not in a state of being pressed, so there is no fear that the projection is deformed. As a result, there is no fear of leakage of blood even if blood is collected and then the blood sampler is placed in the container and the sealing cap is screwed to close the cap, and then blood is stored and transported.

The aspects described above and further aspects, features and advantages of the present disclosure may also be found in the exemplary embodiments which are described in the following with reference to the appended drawings and claims.

BRIEF DESCRIPTION OF DRAWINGS

Further exemplary embodiments of the present disclosure are detailed in the description of the Figures, where this description shall not limit the scope of the present disclosure. The Figures show that.

Throughout the figures, the same reference numerals and characters, unless otherwise stated, are used to denote like features, elements, components or portions of the illustrated embodiments. Moreover, while the subject disclosure will now be described in detail with reference to the figures, it is done so in connection with the illustrative embodiments. It is intended that changes and modifications can be made to the described embodiments without departing from the true scope and spirit of the subject disclosure as defined by the appended claims.

DETAILED DESCRIPTION OF EXEMPLARY EMBODIMENTS

Hereinafter, a blood sampling device and a blood collection method according to embodiments of the present disclosure will be described with reference to the drawings.

The present disclosure will now be described by way of exemplary embodiments, together with preferred methods and materials that can be used in the practice of the present disclosure. Unless otherwise noted in the text, all technical and scientific terms used in the present specification have the same meaning as commonly understood by one of ordinary skill in the art to which this invention belongs. In addition, any materials and methods equivalent or similar to those described in the present specification can be used as well in the practice of the present disclosure. In addition, all publications and patents cited in this specification in relation to the present disclosure described herein constitute a part of the present specification, for example, as methods, materials and the like that can be used with the present disclosure.

In blood tests, blood is prepared by centrifugation according to the purpose, and in this specification, the supernatant component obtained by centrifuging a whole blood sample is defined as serum, and the supernatant component obtained in the anticoagulant-added state is defined as plasma. Furthermore, the precipitated component produced by centrifugation performed to obtain serum or plasma is defined as blood cell.

Hereinafter, a blood sampling device 100 according to the first exemplary embodiment of the present disclosure will be described with reference to FIGS. 1 to 5.

Figure 1:
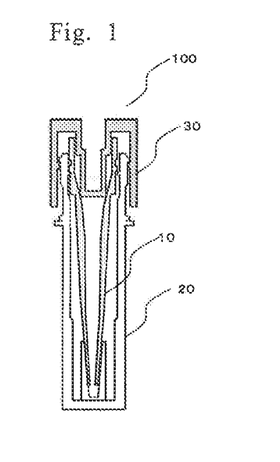
FIG. 1 is a cross-sectional view showing a blood sampling device before blood collection of the present disclosure.

As shown in FIG. 1, the blood sampling device 100 of the e first exemplary embodiment of the present disclosure includes, e.g., a blood sampler 10, a container 20 and a sealing cap 30. The three parts may constitute a blood sampling device as a set in a separate state, but it is preferable that the blood sampler 10 is accommodated in the container 20 and the sealing cap 30 is set in a state of unity as shown in FIG. 1. FIG. 1 shows the state of the blood sampling device 100 before blood collection according to the present disclosure. The blood sampler 10 is inserted into the container 20 and is loosely fixed, and the container 20 and the sealing cap 30 are loosely fitted. The tip of the blood sampler 10 is not in close contact with the bottom surface of the receiving part 21 of the container 20. Therefore, no load is applied to the bottom opening of the blood sampler 10, and deformation of the bottom opening can be prevented. Further, the projection of the locking part 22 of the container 20 and the projection 32 of the sealing cap are engaged with each other to prevent the sealing cap 30 from coming off. In addition, the mandrel 31 of the sealing cap is inserted into the top opening of the blood sampler, and contributes to stability during transportation.

Figure 2:
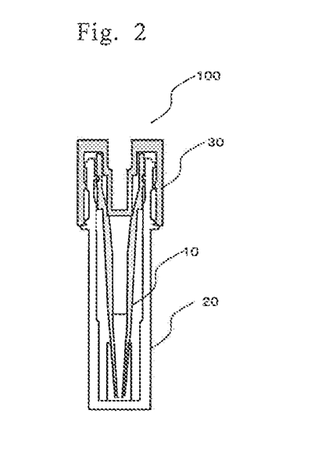
FIG. 2 is a cross-sectional view showing a blood sampling device after blood collection of the present disclosure.

FIG. 2 shows the state of the blood sampling device 100 according to the exemplary embodiment of the present disclosure after blood collection. In this state, the blood sampler 10 after blood collection is placed in the container 20, the sealing cap 30 is fitted, and the container 20 and the sealing cap 30 are screwed together. The bottom opening of the blood sampler 10 is sealed by the close contact between the tip of the blood sampler 10 and the bottom surface of the receiving part 21 of the container 20. Further, in this state, the mandrel 31 of the sealing cap 30 is strongly inserted into the top opening of the blood sampler 10, and the upper inner side of the blood sampler 10 and the mandrel 31 come in close contact with each other to seal the top opening of the blood sampler 10. In addition, the container 20 and the sealing cap 30 are screwed together so that the sealed state is sufficient.

Figure 3:
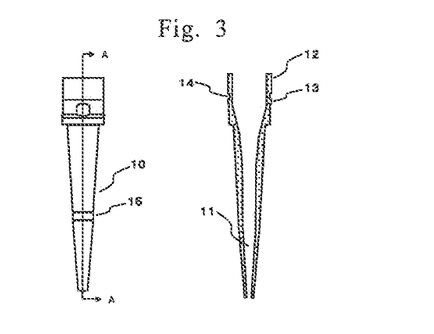
FIG. 3 provides a side view and an A-A cross-sectional view, showing a blood sampler of a blood sampling device of the present disclosure.

FIG. 3 shows the blood sampler 10. The blood sampler 10 has a pipette tip shape and is narrowed toward the tip. The internal space of the blood sampler 10 has a bottom opening and a top opening, which are in communication. The lower part of the internal space constitutes a blood holding part 11 that holds blood, and the blood holding part 11 is tapered from the bottom opening toward the top opening. The ratio of the blood holding part in the internal space is not particularly limited as long as it can hold the target amount of blood, but is preferably about $1/30$ to $4/5$ of the whole, more preferably about $1/10$ to $3/5$ of the whole, further preferably about $1/5$ to $1/2$ of the whole. It is preferable that the upper part 12 close to the upper end of the blood sampler 10 has a cylindrical shape so that its inner side can be in close contact with the root part of the mandrel 31 of the sealing cap, in addition, its outer side can be easily fitted with the container. In addition, the cylindrical shape can facilitate access to the collected blood from the top opening. On the outer side of the upper part 12 of the blood sampler, a convex part 13 and a concave part 14 can be further provided in that order from the tip. The convex part 13 and the concave part 14 are preferably arranged so as to be in opposite positions across the center line. In the side view of FIG. 3, the outer periphery 15 of the lower part of the blood sampler 10 corresponding to the part in contact with the vicinity of the upper end of the receiving part 21 of the container has a shape with no slope. However, it is not necessary to have the outer peripheral part 15 with no slope.

The material of the blood sampler 10 is not limited, but a hard material with high transparency is preferable in consideration of operability and gripping property during blood collecting, and transportability and the like. The blood sampler is preferably made of a material of a polymer compound such as polyvinyl chloride, polyethylene, polypropylene, acrylonitrile butadiene styrene (ABS), polycarbonate, polyethylene terephthalate and the like from the viewpoint of processability, operability and the like.

The volume of the blood holding part 11 of the blood sampler 10 is preferably 200 μL or less, more preferably 150 μL or less, and further preferably 100 μL or less. The inner diameter of the bottom opening of the blood sampler 10 and the inner diameter of the body part that is a blood holding part can be arbitrarily determined as long as the effect of the capillary action can be obtained. The inner diameter of the bottom opening of the blood sampler 10 is, for example, but not limited to, 0.1 mm or more and less than 2.0 mm, preferably 0.3 mm or more and less than 1.5 mm, more preferably 0.5 mm or more and less than 1.0 mm, further preferably 0.7 mm or more and less than 0.9 mm. Thereby, blood can be easily collected from the bottom opening by the capillary action.

The blood holding part 11 has an inner wall preferably subjected to a hydrophilic treatment. When the inner wall is hydrophilically treated, there is an advantage that blood can flow smoothly when blood is collected, and a target amount of blood can be collected easily by combination of the capillary action and the effect of the hydrophilic treatment of the inner wall. The hydrophilic treatment of the inner wall of the blood holding part can be performed using a known method, and hydrophilicity can be imparted by a method including, for example, but not limited to, surface etching, fluorine treatment and introduction of a hydrophilic functional group to the surface via a catalyst. A treatment for imparting hydrophilicity to the surface of a material made of a polymer compound, for example, polypropylene or polycarbonate, is known, and these methods can be used. Although not limited, for example, a method using a mixed gas of a fluorine gas and an oxygen gas or a technique described in Hidehiko Enomoto, Toshiya Murata, Surface Technology, Vol. 59, No. 5, pp. 282-287 (2008) can be used.

An agent can be applied to the inner wall of the blood sampler 10, preferably to the inner wall of the blood holding part 11, as necessary. By collecting blood in the blood sampler 10 in which an agent has been applied to the inner wall, it is possible to add the agent to blood without separately performing an agent addition operation.

Using the exemplary blood sampler 10, blood can be collected from the bottom opening of the blood sampler by utilizing the capillary action or the weight of the liquid itself. For example, when collecting peripheral blood from a fingertip or earlobe, the fingertip or earlobe is punctured, then, the bottom opening of the blood sampler is brought into contact with the blood that has come out, as a result, the blood is introduced into the blood sampler due to the capillary action or the weight of the liquid itself, thus, blood collection is possible.

In the collection of blood, the amount of blood collection by the blood sampler is not limited, and the amount of blood collected can be changed according to the device used, the agent, the purpose of the test item, and the like. When the blood sampling device of the present disclosure is used, it is possible to collect an arbitrary small amount of blood, for example, an arbitrary amount from 10 μL to 300 μL.

Figure 4:
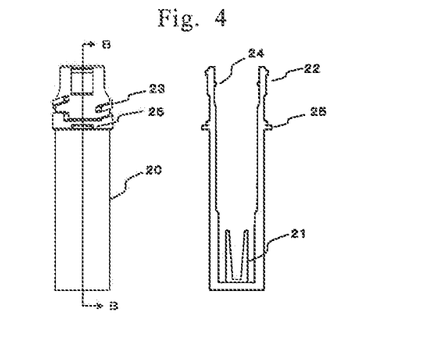
FIG. 4 provides a side view and a B-B cross-sectional view, showing a container of a blood sampling device of the present disclosure.

FIG. 4 shows side and cross-sectional views of the exemplary container 20 according to an exemplary embodiment of the present disclosure. The exemplary container 20 can have a cylindrical internal space into which the blood sampler 10 can be inserted. The bottom part has a receiving part 21 into which the lower part of the blood sampler 10 can be inserted. The receiving part 21 can have a cylindrical shape having substantially the same upper end inner diameter and lower end inner diameter, or may have a shape in which the inner diameter decreases from the upper end to the lower end in accordance with the tip portion of the blood sampler 10. The container 20 has a locking part 22 having a claw-like projection and a screw part 23 on the upper outer side. The locking part and the screw part are arranged so as to be offset from each other in the vertical direction in that order from the upper end of the container 20. A convex part 24 may be further provided on the upper inner side of the container 20. Two convex parts 24 can be preferably arranged at opposing positions. The container 20 can further have a stopper 25 on the outer side for preventing excessive screwing when the sealing cap and the container are screwed together. The stopper 25 can be arranged so as to cover the outer peripheral part, or two stoppers 25 may be arranged so as to be in opposite positions across the center line as shown in the drawing. The length or size of the stopper is not particularly limited, and can be, e.g., as small as a projection as long as it functions as a stopper.

The material of the container 20 is not limited, and it can be preferable that the container 20 is made of (at least in part or in whole) a hard material with high transparency in consideration of operability and gripping property when accommodating the blood sampler, and transportability and the like in accommodation of the blood sampler. The container can be preferably made of a material of a polymer compound such as polyvinyl chloride, polyethylene, polypropylene, acrylonitrile butadiene styrene (ABS), polycarbonate, polyethylene terephthalate and the like from the viewpoint of processability, operability and the like.

Figure 5:
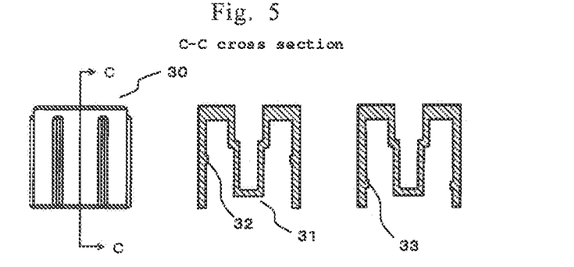
FIG. 5 provides a side view, a C-C cross-sectional view and a cross-sectional view at a position 90° to the C-C plane, showing a sealing cap of a blood sampling device of the present disclosure.

FIG. 5 shows side and cross-sectional view of the sealing cap 30 according to the exemplary embodiment of the present disclosure. The sealing cap 30 can have a cap piston shape. A mandrel 31 extends from the inner upper surface of the sealing cap. The upper end of the mandrel can be opened or closed. The shape of the mandrel is not particularly limited, and may be a cylindrical shape in which the diameter of the root part extending from the inside of the sealing cap and the diameter at the tip are approximately the same or may be a stepped shape in which the diameter of the root part is larger than the diameter of the tip, and the latter can be preferable. In the latter exemplary case, when the blood sampler is accommodated in the container after blood collection, the root part of the mandrel can be brought into closely contact with the upper inner side of the blood sampler and the tip of the mandrel can be strongly pushed into the blood sampler, to improve sealing performance. A projection 32 and a screw part 33 can be provided on the inner side surface of the sealing cap. The projection 32 and the screw part 33 can be arranged so as to be offset from each other in the vertical direction in that order from the upper end of the sealing cap.

The material of the sealing cap is not limited, and it can be preferable that the sealing cap is a hard material with high transparency in consideration of gripping property by the operator, transportability and the like. The sealing cap can be preferably made of a material of a polymer compound such as polyvinyl chloride, polyethylene, polypropylene, acrylonitrile butadiene styrene (ABS), polycarbonate, polyethylene terephthalate and the like from the viewpoint of processability, operability and the like.

The assembly of the blood sampling device 100 according to the exemplary embodiment of the present disclosure, before blood collection, can be in a state of unity, whereas the blood sampler 10 can be accommodated in the container 20 and the sealing cap 30 is set will be described.

As shown in FIG. 1, the exemplary blood sampling device 100 before blood collection can be so constituted such that the blood sampler 10 is inserted into the container 20, the blood sampler 10 is loosely fixed in the container 20, and further, the sealing cap 30 is loosely fitted to the container 20. A convex part 13 and a concave part 14 may be provided on the upper outer side of the blood sampler, and a convex part 24 may be provided on the upper inner side of the container. In such a case, when the blood sampler 10 is inserted into the container 20, the convex part 13 of the blood sampler collides with the convex part 14 of the container, thereby preventing the blood sampler from being excessively inserted into the container, and the blood sampler can be easily loosely fitted into the container. After inserting the blood sampler 10 into the container 20, if the screw part 23 of the container 20 and the screw part 33 of the sealing cap 30 or the locking part 22 and the projection 32 are aligned and the sealing cap 30 is fitted in the container 20, the projection 32 on the inner side of the sealing cap collides with the locking part 22 on the outer side of the container. When the sealing cap is further pushed in, the screw part 33 on the inner side of the sealing cap collides with the screw part 23 on the outer side of the container to serve as a stopper, thereby preventing the sealing cap from being pushed further. In this exemplary state, the projection 32 and the locking part 22 can be engaged with each other, thus, it can serve to prevent the sealing cap from coming off, and the container 20 and the sealing cap 30 can be loosely fixed to each other. Further, the mandrel 31 extending from the inner upper surface of the sealing cap is located in the upper part of the internal space of the blood sampler 10. As described above, the blood sampling device 100 before blood collection can be configured in a state in which the sealing cap is not dropped off and the blood sampler, the container and the sealing cap are loosely fitted, thus, since they are grouped together, the handling of the device is easy.

For the blood sampling device 100 according to the exemplary embodiment of the present disclosure, e.g., the blood sampler 10, the container 20 and the sealing cap 30 may be placed in a separate state before blood collection, and such exemplary configuration can also be provided in the blood sampling device 100 in the exemplary embodiment of the present disclosure. In such exemplary case, it can be preferable that those parts are stored in a case or the like that can fix those parts.

Further, blood collection is further described herein. For blood collection, the blood sampler 10 can be removed from the exemplary blood sampling device 100 before blood collection, alternatively, when parts are stored in a separate state in a case, the blood sampler 10 is taken out from the case, and the tip can be brought into contact with blood, to carry out blood collection. The blood collection with the blood sampler 10 is described herein with reference to FIG. 8. While the drawing shows blood collection when the blood sampler 10 and the container 20 are combined, the same can apply to the exemplary case where only the blood sampler 10 is used.

Figure 8:
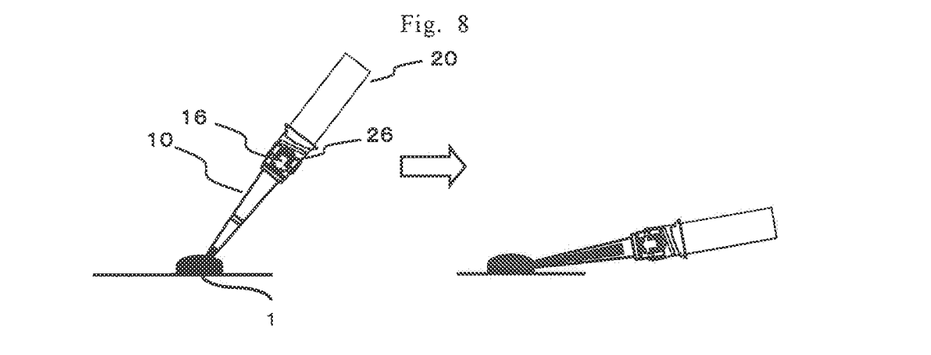
FIG. 8 is an explanatory view showing a state in which blood is collected using a blood collection tool in which a blood sampler and a container are combined, using a blood sampling device according to the second embodiment of the present disclosure.

For example, blood collection using the blood sampler 10 can be performed by picking the outer periphery of the top opening of the blood sampler with fingers and bringing the bottom opening into contact with blood. Alternatively or in addition, as shown in FIG. 8, by fitting the upper end of the blood sampler to the upper end of the container while the blood sampler is turned upside down, a blood collection tool for collecting blood consisting of the blood sampler 10 and the container 20 is provided. In such exemplary blood collection tool, blood can be collected by picking the outer periphery of the container with fingers and bringing the bottom opening into contact with blood, so it can be easier to handle.

When blood is collected, by bringing the tip of the blood sampler 10 into contact with blood 1, blood suction is started by the capillary action and/or the weight of the liquid itself, and the blood is aspirated and filled in the blood holding part 11, as shown in FIG. 8. FIG. 8 illustrates that the blood sampler 10 is tilted horizontally, this making it possible to collect a larger amount of blood more easily. Further, if a target amount of blood can be collected, it does not have to be tilted. The blood collected using the blood sampling device of the present disclosure can be preferably peripheral blood.

The amount of blood to be collected can be changed according to the intended examination and measurement, and the length and diameter of the blood holding part 11 can be adjusted accordingly. For example, the amount of blood to be collected can be adjusted, and not limited thereto, in the range of 10 µL to 300 µL, preferably 10 µL to 200 µL, more preferably 50 µL to 100 µL. Further, by providing the blood sampler with a guide line indicating that a specific amount of blood has been collected, it is possible to accurately collect a specific amount of blood.

The collected blood can be held in the exemplary blood holding part 11. The hollow structure inside the blood holding part 11 has a taper shape, and this taper shape improves the suction of blood by inducing the weight of the liquid itself in addition to the capillary action when blood is collected from the lower part. The blood holding part 11 can have a capillary action and a function of the weight of the liquid itself, and may have any outer shape, inner shape and material as long as the blood can be collected from the upper part, and by using a hydrophilic material or a hydrophilically-treated material on the inner surface, a better capillary action can be achieved.

After collecting blood, the exemplary blood sampler 10 can be inserted into the container 20. After blood collection, by strongly pushing the blood sampler into the container, the lower part of the blood sampler is fitted into the receiving part 21 of the container and the upper part of the blood sampler is fitted to the upper inner side of the container. If the receiving part 21 has a cylindrical shape having approximately the same upper end inner diameter and lower end inner diameter, the vicinity of the upper end of the receiving part 21 and a part of the lower part of the blood sampler 10 can come into close contact and may be fitted with each other. In such exemplary case, the outer periphery 15 at the lower part of the blood sampler 10 corresponding to the part in contact with the vicinity of the upper end of the receiving part 21 can be formed into a shape having no slope in order to ensure the close contact. When the convex part 13 and the concave part 14 are provided on the upper outer side of the blood sampler and the convex part 24 is provided on the upper inner side of the container, the concave part 14 and the convex part 24 can be fitted together by inserting the blood sampler 10 into the container 20 and pressing it strongly. Next, the sealing cap 30 can be fitted and further screwed. In this state, the bottom opening of the blood sampler is completely closed by the receiving part 21, while the top opening is completely closed by the mandrel 31 of the sealing cap, and the blood sampler holding blood in the blood holding part can be completely sealed. FIG. 2 shows a cross-section of the exemplary blood sampling device 100 in this exemplary mode.

Even if the exemplary blood sampler 10 after blood collection is not pushed strongly into the container 20, by fitting and further screwing the sealing cap 30, the lower part of the blood sampler is fitted into the receiving part 21 of the container and the upper part of the blood sampler is fitted to the upper inner side of the container, and the bottom opening of the blood sampler is closed completely by the receiving part 21 and the top opening is closed completely by the mandrel of the sealing cap, to completely seal the blood sampler holding blood in the blood holding part.

Figure 6:
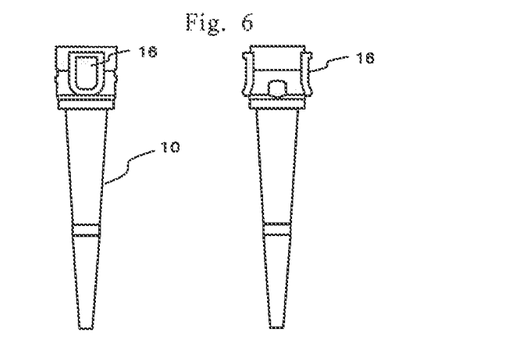
FIG. 6 provides a front view and a side view, showing a blood sampler of a blood sampling device according to the second embodiment of the present disclosure. A U-shaped projection is disposed on the upper part of the blood sampler.
Figure 7:
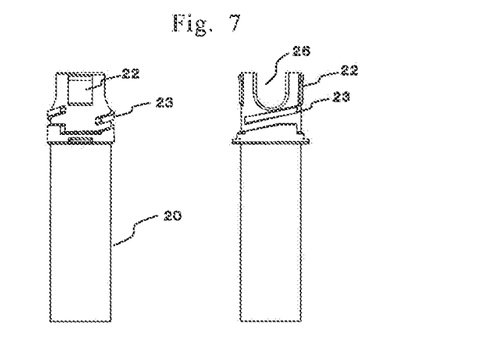
FIG. 7 provides a front view and a side view, showing a container of a blood sampling device according to the second embodiment of the present disclosure. A U-shaped notch is disposed on the upper part of the container.

FIGS. 6 and 7 illustrate side views of the exemplary blood sampler 10 and the exemplary container 20 of the blood sampling device 100 according the second exemplary embodiment of the present disclosure. In the second exemplary embodiment, the blood sampler 10 has a U-shaped projection 16 at the top thereof, while the container 20 has a U-shaped notch 26 that fits with the projection 16 at the top thereof. Preferably, two U-shaped projections 16 and two U-shaped notches 26 can be arranged, respectively. With this exemplary configuration, in the blood sampling device 100 before blood collection, a part of the U-shaped projection 16 and a part of the U-shaped notch 26 are engaged, to help loose fixation of the blood sampler and the container. Then, in the blood sampling device 100 after blood collection, the U-shaped projection 16 and the U-shaped notch 26 are engaged to help the blood sampler and the container to be firmly fixed.

In blood collection in the blood sampling device according to the second exemplary embodiment, by taking the blood sampler 10 out of the container 20 and turning it upside down and inserting the U-shaped projection of the blood sampler 10 into the U-shaped notch of the container 20, a blood collection tool in which a part of the U-shaped projection and a part of the U-shaped notch can be fitted to each other can be produced. A blood collection tool in which the blood sampler 10 and the container 20 can be combined can be easily grasped and can collect blood by an easier operation. For example, in the blood sampling device 100 of the second embodiment, blood can also be collected using only the blood sampler 10.

Figure 9:
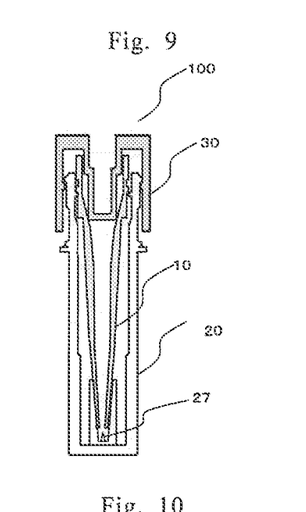
FIG. 9 is a cross-sectional view showing a blood sampling device according to the third embodiment of the present disclosure.

FIG. 9 is a cross-sectional view of the blood sampling device 100 according to the third exemplary embodiment of the present disclosure. In the third exemplary embodiment, the bottom surface of the receiving part 21 of the container 20 can be provided with a projection 27 that matches the diameter of the bottom opening of the blood sampler 10. The exemplary blood sampling device of the present disclosure before blood collection can be in a state where the blood sampler 10 is inserted into the container 20 and is loosely fixed and the container 20 and the sealing cap 30 are loosely fitted, thus, the bottom opening of the blood sampler 10 is not in close contact with the projection. Therefore, even if it is stored and transported in a unit state before blood collection, the deformation of the projection can be prevented. After blood collection, in an exemplary state where the blood sampler 10 is inserted into the container 20 and the sealing cap 30 is fitted and screwed together, the projection 27 can be inserted into the bottom opening of the blood sampler 10 and the bottom opening comes into close contact with the projection 27. As a result, better sealing can be achieved.

The blood sampling device according to the exemplary embodiments of the present disclosure can be stored and/or transported with a blood sampler containing blood inserted in the container. Moreover, the blood sampling device of the present disclosure can be subjected to a centrifugal separation operation in a state where the blood sampler is inserted into the container. Thus, the blood can be centrifuged in a state where the blood is held in the blood sampling device of the present disclosure, and separated into serum or plasma and blood cells, and the device can be stored and/or transported as it is. Furthermore, with the exemplary blood sampling device according to the exemplary embodiments of the present disclosure, a centrifugal separation operation is conducted, then, the sealing cap is opened, and the resultant supernatant (serum or plasma) can be collected by a collecting arrangement/device (for example, a micropipette).

The blood sampling device 100 according to the exemplary embodiments of the present disclosure can have a configuration in which the blood sampler 10 that has collected blood is inserted into the container 20 and the sealing cap 30 is fitted and screwed, so that the blood is sealed and sufficient sealing is attained not only under atmospheric pressure but also under negative pressure. Further, in this exemplary state, it can be stored or transported, and further, it can also be centrifuged.

Figure 10:
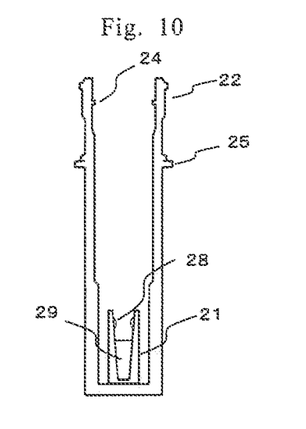
FIG. 10 shows an embodiment in which an agent is added to a receiving part of a container using a blood sampling device of the present disclosure.

In the blood sampling device 100 according to the exemplary embodiment of the present disclosure, an agent can be added to the receiving part 21 in advance according to the blood collecting conditions. When the blood sampler 10 that has collected blood is inserted into the container 20 and pushed in, or when the blood sampler 10 that has collected blood is inserted into the container 20 and the sealing cap is fitted and screwed, the agent 29 flows in the blood sampler, then, the tip of the blood sampler is sealed. Thereby, the blood to which the agent is added can be prepared without separately performing an agent addition operation. As shown in FIG. 10, when the agent 29 is held in the receiving part 21, it is preferable to provide a lock mechanism 28 in the receiving part. By providing the lock mechanism, when the tip of the blood sampler 10 is inserted into the receiving part 21 of the container 20, the leakage of the agent into the container can be prevented and the inflow of the agent into the blood sampler can be sufficient.

The agent is appropriately selected according to the purpose, and includes, for example, but not limited to, a separating agent. The type of the separating agent that can be used in the exemplary embodiments of the present disclosure is not particularly limited, and can include those composed mainly of, for example, silicon, α-olefin-maleic acid ester, polyester polymer, acrylic polymer, chlorinated polybutene and cyclopentadiene resins, or modified cyclopentadiene resins obtained by introducing a hydroxyl group, an ester group, an ether group, an epoxy group and the like into cyclopentadiene resins, and the like.

In the exemplary blood sampling device 100 according to the exemplary embodiments of the present disclosure, it is possible that an agent is applied in advance to the inner wall of the blood sampler 10, e.g., preferably to the inner wall of the blood holding part 11 in accordance with the blood collecting conditions. The agent that can be applied is appropriately selected according to the purpose and includes, for example, but not limited to, an anticoagulant, a procoagulant and a glycolytic inhibitor. For example, the anticoagulant can be added for the purpose of collecting plasma, the procoagulant may be added for the purpose of shortening the clotting time when collecting serum, and the glycolytic inhibitor may be added to consume glucose in blood when cells such as red blood cells are present, and to inhibit glycolysis thereof.

When blood is collected using the exemplary blood sampler 10, blood comes into contact with the agent applied to the inner wall, and the agent diffuses into the blood. In order to promote mixing of the agent and blood, it can be preferable to insert the exemplary blood sampler 10 into the exemplary container 20 and screw the sealing cap 30, and then to invert the device to mix them. The number of times of inversion mixing is not particularly limited as long as mixing can be sufficiently achieved, and it is usually performed several times, preferably 5 times or more. By applying the agent to the inner wall, it is possible to prepare blood to which the agent has been added without separately performing an agent addition operation after blood collection.

In the exemplary embodiment added with the anticoagulant according to the present disclosure, the coagulation of blood can be inhibited by the anticoagulant, so it can be stored or transported immediately after blood collection without separating plasma and blood cells by centrifugation. It is also possible to separate the plasma and blood cells by centrifugation. The type of the anticoagulant that can be used in the present disclosure is not particularly limited, and examples thereof include ethylenediaminetetraacetic acid (EDTA) alkali metal salts, heparin alkali metal salts, or sodium citrate and the like.

The type of the procoagulant that can be used in the present disclosure is not particularly limited, and examples thereof include silica fine particles, thrombin and the like.

The type of the glycolytic inhinbitor that can be used with the exemplary embodiments of the present disclosure is not particularly limited, and examples thereof include sodium fluoride and the like.

In the blood sampling device 100 according to the exemplary embodiments of the present disclosure, information for identifying the blood sampling device 100 may be added to the container 20 or the sealing cap 30 as long as the collected blood is not affected. For example, information can be added to the blood sampling device 100 after blood collection or before blood collection, by attaching a sticker printed with an ID or a one-dimensional bar-code produced based on the ID to the container 20 or the sealing cap 30, for identifying each blood sampling device 100.

When the blood sampling device according to the exemplary embodiments of the present disclosure is used, good blood suitable for blood analysis can be prepared even with a small amount of peripheral blood collected from a fingertip or earlobe and the like. Such blood can be diluted and analyzed by a conventional protocol used for analysis of brachial venous blood collected with a conventional blood collection tube or the like, a method described in a publication, e.g., Hajime Iwasawa et al., "Correlation of the blood test results obtained between assays using microliter-scale fingertip blood samples collected with a novel blood collection device and conventional venous blood assays", Clinical Pathology 2017; 65 (3): 252-259. and Shihoko Namba et al., A New Hepatitis Virus Test with Microliter-scale Fingertip Blood Collection in Japan, Acta Med. Okayama 208; 72 (3): 283-287, and the like, or with an existing analyzer. For example, the blood analysis similar to the conventional analysis can be performed using a small amount of peripheral blood collected from a fingertip or earlobe. Although not limited thereto, for example, when 60 μL, of whole blood is collected from a fingertip and serum or plasma is prepared using the blood sampling device of the present disclosure, about 30 μL, of serum or plasma can be obtained. When this is diluted 10-fold with a dilution buffer (for example, physiological saline), a 300 μL, blood sample can be prepared. Using this, normal biochemical analysis of blood can be performed. That is, the present disclosure is also a blood sampling device which can be used for conducting blood analysis using a small amount (for example, 300 μL, or less, preferably 100 μL or less, more preferably 60 μL, or less) of peripheral blood collected from a fingertip or earlobe. For example, blood collected using the blood sampling device of the present disclosure can also be used for special test items such as cancer markers and allergies, in addition to general biochemical item and/or immune item tests commonly used in blood tests, so-called blood biochemical tests.

The above description is merely illustrative of the exemplary objects and subjects of the present disclosure and is not intended to limit the scope of the appended claims. Various changes and substitutions to the described exemplary embodiments will be apparent to those skilled in the art from the teachings set forth in the present specification without departing from the scope of the appended claims.

EXEMPLARY DESCRIPTION OF NUMERALS

Provided below are exemplary descriptions of certain elements and/or parts shown in the drawings, which are certainly non-limiting, and merely exemplary, as follows:
1. blood
10. blood sampler
11. blood holding part
12. blood sampler upper part
13. blood sampler convex part
14. blood sampler concave part
15. blood sampler lower periphery
16. U-shaped projection
20. container
21. receiving part
22. locking part
23. screw part
26. U-shaped notch
27. projection
28. lock mechanism
29. agent
30. sealing cap
31. mandrel
32. projection
33. screw part
100. blood sampling device

The invention claimed is:

1. A blood sampling device comprising:
a pipette tip-shaped blood sampler having a first internal space for holding blood after aspirating the blood and having openings at the top and bottom;
a cylindrical container capable of accommodating the blood sampler; and
a cap piston-shaped sealing cap for sealing the container, wherein:
the first internal space of the blood sampler is configured such that the openings at the top and the bottom communicate with one another,
a lower part of the first internal space constituting a blood holding part has a tapered shape,
blood is aspirated into the first internal space by the capillary action when the opening at the bottom is brought into contact with blood,
the container has (i) a second internal space into which the blood sampler is insertable, (ii) a receiving part at the bottom into which a tip of the blood sampler is insertable, (iii) a locking part having a claw-like first projection and a first screw part are provided on an upper outer side of the container, and (iv) the locking part and the first screw part are arranged to be offset from each other in a vertical direction in that order from the top of the container, and
the sealing cap has (i) a mandrel extending from an inner upper surface of the sealing cap to the first internal space of the blood sampler, (ii) a second projection that engages with the first projection of the locking part of the container, and (iii) a second screw part connectable to the first screw part of the container provided on an inner side surface of the sealing cap, and the second projection and the second screw part are arranged to be offset from each other in the vertical direction in that order from the top of the sealing cap.

2. The blood sampling device according to claim 1, wherein the locking part and the first screw part of the container and the second projection and the second screw part of the sealing cap are configured such that when the sealing cap is attached to an upper end of the container, the second screw part of the sealing cap and the first screw part of the container come into contact with each other and serve as a stopper by which the container is uninsertable into the sealing cap, and the first projection of the locking part engages with the second projection of the sealing cap to prevent the sealing cap from being removed, and wherein the sealing cap is loosely fitted to the upper end of the container.

3. The blood sampling device according to claim 1, wherein, when the sealing cap is fitted into an upper part of the container and the second screw part of the sealing cap and the first screw part of the container are connected together under condition where the blood sampler that has collected blood is inserted into the container, the tip of the blood sampler is further fitted into the receiving part of the container and the mandrel of the sealing cap is inserted into a top opening of the blood sampler to close the top opening and the bottom opening of the blood sampler and to seal the container into which the blood sampler holding blood is inserted.

4. The blood sampling device according to claim 1, wherein two of the locking part and two of the first screw part are arranged at an upper part of the container and two of the second projection and two of the second screw part are arranged on the sealing cap, respectively.

5. The blood sampling device according to claim 1, wherein the blood sampler has a U-shaped projection at an upper part thereof, and the container has a U-shaped notch that that serves as a guide and fits to the U-shaped projection at the upper part.

6. The blood sampling device according to claim 1, wherein an inner wall of a lower part of the first internal space of the blood sampler constituting the blood holding part is hydrophilically treated.

7. The blood sampling device according to claim 6, wherein the hydrophilic treatment of the blood sampler is performed by etching or fluorine treatment.

8. The blood sampling device according to claim 1, wherein the opening at the bottom of the blood sampler is an opening having an inner diameter of approximately 0.5 mm or more and less than approximately 1.0 mm.

9. The blood sampling device according to claim 1, wherein a bottom surface of the receiving part of the container has a third projection that fits into the opening at the bottom of the blood sampler.

10. The blood sampling device according to claim 1, wherein the receiving part of the container includes an agent that is added thereto.

11. The blood sampling device according to claim 10, wherein the agent is a separating agent.

12. The blood sampling device according to claim 1, further comprising an agent that is applied to an inner wall of the blood holding part.

13. The blood sampling device according to claim 12, wherein the agent is selected from the group consisting of anticoagulants, procoagulants and glycolytic inhibitors.

14. The blood sampling device according to claim 1, wherein the locking part and the first screw part are arranged to be offset from each other in a horizontal direction of the container.

15. The blood sampling device according to claim 1, wherein the second projection and the second screw part are arranged to be offset from each other in a horizontal direction of the sealing cap.

* * * * *